(12) United States Patent
Domb

(10) Patent No.: US 7,297,347 B2
(45) Date of Patent: Nov. 20, 2007

(54) POLYANHYDRIDES

(75) Inventor: Abraham J. Domb, Efrat (IL)

(73) Assignee: Efrat Biopolymers Ltd, Efrat (IL)

( * ) Notice: Subject to any disclaimer, the term of this patent is extended or adjusted under 35 U.S.C. 154(b) by 286 days.

(21) Appl. No.: 10/433,143

(22) PCT Filed: Nov. 27, 2001

(86) PCT No.: PCT/IL01/01103

§ 371 (c)(1),
(2), (4) Date: May 30, 2003

(87) PCT Pub. No.: WO02/44232

PCT Pub. Date: Jun. 6, 2002

(65) Prior Publication Data

US 2004/0057970 A1    Mar. 25, 2004

(30) Foreign Application Priority Data

Nov. 30, 2000   (IL) .................................... 140017

(51) Int. Cl.
*A61K 9/36*   (2006.01)
*C08G 63/00*  (2006.01)

(52) U.S. Cl. .............. 424/484; 424/485; 424/486; 528/205; 528/271

(58) Field of Classification Search ............ 424/428, 424/489, 490, 484–486; 528/271, 206, 205, 528/328, 350, 274
See application file for complete search history.

(56) References Cited

U.S. PATENT DOCUMENTS

| 4,999,417 | A | * | 3/1991 | Domb ............... 528/271 |
| 5,010,167 | A | * | 4/1991 | Ron et al. ........... 528/328 |
| 5,109,107 | A | * | 4/1992 | Vora et al. .......... 528/350 |
| 5,171,812 | A | * | 12/1992 | Domb ............... 526/318.2 |
| 5,179,189 | A | * | 1/1993 | Domb et al. ........ 528/271 |
| 5,317,079 | A | * | 5/1994 | Domb et al. ........ 528/271 |

FOREIGN PATENT DOCUMENTS

| EP | 0 598 131 | | 5/1994 |
| WO | WO90/15586 T | * | 12/1990 |
| WO | WO 93/05096 | | 3/1993 |
| WO | WO 96/22270 | | 7/1996 |
| WO | WO99/12990 | * | 3/1999 |
| WO | WO 99/12990 A2 | * | 3/1999 |

* cited by examiner

*Primary Examiner*—Michael G. Hartley
*Assistant Examiner*—Micah-Paul Young
(74) *Attorney, Agent, or Firm*—Pabst Patent Group LLP

(57) ABSTRACT

The invention provides polyanhydrides with aliphatic hydrocarbon terminals having ester or amide bonds.

31 Claims, No Drawings

POLYANHYDRIDES

Priority is claimed under 35 U.S.C. § 119 to PCT/IL01/01103, filed Nov. 27, 2001, which claims priority to Israeli Patent Application No. 140,017, filed Nov. 30, 2000.

The present invention relates to polymers for controlled delivery of substances, and more specifically encompasses biodegradable polyanhydrides with ester and amide bonds and methods for making the same.

There has been extensive research in the area of biodegradable materials for controlled release of drugs. Biodegradable matrices for drug delivery are useful because they obviate the need to remove non-degradable drug depleted devices. The ideal polymeric matrix would combine the characteristics of hydrophobicity, storage stability, solubility in organic solvents, melting point below 100° C. to allow injection molding processing, predetermined controlled degradation profile, versatile degradation and drug release profiles, and flexible and non-fragile so that it does not crumble or fragment during shipment or use.

Such a polymer must be hydrophobic so that it retains its integrity and the incorporated drug for a suitable period of time when placed in biological systems, such as the body, and stable at common storage conditions, preferable room temperature for an extended period before use.

Controlled release devices are typically prepared in one of several ways. For example, the polymer can be melted, mixed with the active substance and cast,or injection mold into a device. Such melt fabrication require polymers having a melting point that is below the temperature at which the substance to be delivered and polymer degrade or become reactive. The device can be prepared by solvent casting where the polymer is dissolved in a solvent and the drug dissolved or dispersed in the polymer solution and the solvent is evaporated. Solvent process requires that the polymer be soluble in organic solvents. Another method is the compression molding of mixed powders of the polymer and the drug or polymer particles loaded with the active agent.

Many biodegradable polymers have been evaluated for their suitability for use as a matrix for drugs including polyesters, polycarbonates, natural and synthetic polyamides, polyphosphate esters, polyphosphazenes and polyanhydrides. While these polymers were found useful applications as drug carriers, still there is a need for a reliable polymer for short term drug release (1 to 20 weeks) that degrade and eliminated from an implant site within 30 weeks.

Polyanhydrides are useful bioabsorbable materials for controlled drug delivery. They hydrolyze to dicarboxylic acid monomers when placed in aqueous medium. Since their introduction to the field of controlled drug delivery, about 15 years ago, extensive research has been conducted to study their chemistry as well as their toxicity and medical applications. Several review articles have been published on polyanhydrides for controlled drug delivery applications (Domb et al. 1992, Leong et al. 1989, Laurencin 1995).

Since the discovery of polyanhydrides in 1909, hundreds of polymer structures have been reported (Encyclopedia 1969). Polyanhydrides intended for use in medicine that have been developed since 1980 include: Unsaturated polymer prepared from fumaric acid; Amino acid based polymers; Aliphatic-Aromatic homopolyanhydrides; Poly(ester-anhydrides) made from di- and tri-block copolymers of poly(caprolactone); and ester containing polyanhydride.

The stability of polyanhydrides in solid state and dry chloroform solution was studied (Domb and Langer 1989b). Polyanhydrides such as PSA decreased in molecular weight over time. The decrease in molecular weight shows first-order kinetics, with activation energies of 7.5 Kcal/mole- ° K. The decrease in molecular weight was explained by an internal anhydride interchange mechanism, as revealed from elemental and spectral analysis. A similar decrease in molecular weight as function of time was also observed among the aliphatic-aromatic co-polyanhydrides and imide containing co-polyanhydrides. (Domb et al. 1989, Staubli et al. 1991, 1991b).

The low melting point and the solubility of aliphatic polyanhydrides in common organic solvents such as methylene chloride, allows for the easy dispersion of drug into the polymer matrix. Drugs can also be incorporated via compression or melt molding processes. For example, drugs can be incorporated into a slab either by melt mixing the drug into the melted polymer or by solvent casting. Polymer slabs loaded with a drug can also be prepared by compression molding a powder containing the drug. Similarly, one can injection molded the drug-polymer formulation into beads or rods polymer films can be prepared by solvent evaporation by casting the polymer solution containing the drug onto a Teflon coated dish. Microspheres based delivery systems can be formulated by the common techniques including solvent removal, hot-melt encapsulation and spray drying (Mathiowitz et al. 1987, Pekarek et al. 1994, Bindschaedler et al. 1988, Tabata et al. 1994). However, it is essential that all processes be performed under anhydrous conditions to avoid hydrolysis of the polymer or absorption of water in the polymer mass which degrade the polymer with time during storage.

The degradation of polyanhydrides, in general, varies with a number of factors. These factors include, the chemical nature and the hydrophobicity of the monomers used to produce the polymer, the level of drug loading in the polymeric matrix, the pH of the surrounding medium (the higher the pH, the more rapidly the polymers degrade), the shape and geometry of the implant (the degradation is a function of the surface area) and the accessibility of the implant to water (porous materials will degrade more rapidly than non-porous). The porosity in an implant is dependent on the method of fabrication. For example, a compression-molded device will degrade at a much more rapid rate than an injection molded device due to the presence of a higher porosity in the polymer as compared to the latter.

The degradation rates for a number of polyanhydrides are available in the literature (Leong et al. 1986, Shieh et al. 1994, Domb et al. 1995b, Tamada and Langer 1993, Dang et al. 1996). Most studies focused on the degradation of the clinically tested polyanhydrides namely, poly(CPP-SA) and poly(FAD-SA). In general, during the initial 10 to 24 hours of water incubation in aqueous medium, the molecular weight dropped rapidly with no loss in wafer mass loss. This period was followed by a fast decrease in wafer mass accompanied by a very small change in polymer molecular weight. The period of extensive mass loss starts when the polymer molecular weight reaches a number average molecular weight (Mn) of about 2,000 regardless of the initial molecular weight of the polymer. During this period which last for about one week, sebacic acid, the relatively water soluble comonomer, is released from the wafer leaving the less soluble comonomer, CPP or FAD, which is slow to soluble (Dang et al. 1996) increasing the content of sebacic acid in the copolymer increases the hydrophilicity of the copolymer, which results in a higher erosion rate and hence higher drug release rates. This could be explained by the fact that the anhydride linkages in the polymer are hydrolyzed subsequent to penetration of water into the polymer. The penetration of water or water uptake depends on the hydrophobicity of the polymer and therefore, the hydrophobic polymers which prevent water uptake, have slower erosion rates and lower drug release rates. This is valuable information since one can alter the hydrophobicity of the polymer by altering the structure and/or the content of the copolymer, thereby being able to alter the drug release rate. Since in the P(CPP-SA) and P(FAD-SA) series of copolymers, a 10 fold increase in drug release rate was achieved by alteration of the ratio of the monomers, both polymers can be used to deliver drugs over a wide range of release rates.

Several attempts were made to improve the physical properties, drug release and storage stability of polyanhydrides by using fatty acid based comonomers, using linear fatty acid chain terminals or by blending the polymers with fats and other biodegradable polymers. U.S. Pat. No. 5,171,812 and (Domb et al. 1993). describes the synthesis of polyanhydrides from dimer and trimer erucic acid. Theses polymers were amorphous with a crystallinity in the range of 20%, they were hydrophobic and pliable and released the incorporated drugs for a few weeks in buffer solutions. However, these dimer fatty acid based polymers were not stable on storage at room temperature or refrigeration and rapidly decreased in molecular weight which requires storage under freezing conditions (−20° C.). Another major problem occurred with this class of polymers is their incomplete degradation and elimination from dogs after subcutaneous or intramuscular implantation probably due to the C—C bond between the two connected fatty acids.

To solve the problem of the FAD polymer elimination in vivo, diacid fat with hydrolyzable ester bond has been synthesized and evaluated as carrier for drugs. Polyanhydrides synthesized from nonlinear hydrophobic fatty acid esters based on ricinoleic, maleic acid and sebacic acid, possessed desired physico-chemical properties such as low melting point, hydrophobicity and flexibility to the polymer formed in addition to biocompatibility and biodegradability. (Domb et al. 1995). Although these polymers showed to be fully degradable in vivo with suitable properties as drug carriers, the major problem of storage stability and the high polydispersity remain. These polymers' molecular weight was drastically decrease within 2-3 days when stored at room temperature and the polydispersity was over 10.

Another attempt to obtain stable polyanhydrides that are useful for controlled drug delivery was the formation of polyanhydrides with linear fatty acid terminals (U.S. Pat. No. 5,179,189). This invention describes linear polyanhydrides made of aliphatic or aromatic diacids terminated with linear fatty acids such as stearic acid. Although these polymers posses longer drug release period and degradation time, they remain crystalline (>50%) and not pliable similar to the corresponding polymers with acid or acetyl terminals. More important, the polymers are not stable at room temperature or at refrigeration and depolymerize and hydrolyze to a low molecular weight polymer a few days of storage and form a fragile and easy to crumble polymer mass. Another attempt was the blending of polyanhydrides with biodegradable polyesters or fatty acids and triglycerides (Abuganima 1996, Domb 1993c). The resulted polymeric mixtures did not form uniform blends, the polyanhydride component in the mixture degraded at a similar rate as the pure polymer leaving the hydrophobic component intact, and the storage stability did not improve.

While hundreds of polyanhydride structures are available for use as drug carriers, they suffer from a few major limitations as practical carriers for drugs: 1. many of them are made of synthetic monomers such as aromatic and heterocyclic diacid monomers which present a risk of toxicity and slow elimination rate from an implanted animal or human (these hydrophobic co-monomers are used to control the drug release and polymer degradation); 2. high sensitivity to heat and moisture which makes these polymers unstable at room temperature or even at refrigeration storage conditions which require storage at −20° C. or below. This storage stability problem is essential for a medical product to be distributed to hospitals, distribution and storage at −20° C. is very difficult logistically, expensive and somewhat impractical. The only polyanhydride device in clinical use is the Gliadel brain implant which is manufactured by Guilford Pharm. Baltimore which requires an all time storage at −20° C. as at higher temperature the molecular weight of the polymer carrier drops to below 20,000 which affect the drug release rate and rejection of the device; 3 polymers made of linear aliphatic acids are crystalline and fragile which makes them impractical for use as drug carriers as they may fragment during shipment or use.

There remains a strong need for a polymer having the desired characteristics of hydrophobicity, pliability, low melting point and solubility in solvents, versatility in polymer degradation and drug release profile which are stable at non freezing conditions.

It is therefore the objective of this invention to provide a new class of biodegradable polyanhydrides that posses the above desired characteristics with storage stability at non-freezing storage conditions (>0° C.).

It is further the objective of this invention to provide polymers that are easily produced from natural acids that degrade into natural non-toxic acids; It is further the objective of this invention to provide polymers that release drug at a predetermined controlled manner from one to twenty weeks and eliminate from a body of an implanted animal within 30 weeks.

It is further the objective of this invention to provide polymers with a controlled molecular weight and polydispersity below 4 that can be fabricated by melt molding or solvent cast into flexible microparticles, beads films or rods; It is further the objective of this invention to provide polymers that are processable by injection molding;

It is further the objective of this invention to provide polymers with a range of hydrophobicities and flexibility that degrade and release an incorporated drug for weeks by altering the polymer terminals without the need to replace the main chain monomers;

It is further the objective of this invention to provide polyanhydrides with amide and ester bonds that are prepared by reacting hydroxy acids or amino acids with a polyanhydride and repolymerized to a form an ester-anhydride or amide-anhydride polymers;

It is further the objective of this invention to provide polymers that are stable to g-irradiation sterilization.

SUMMARY OF THE INVENTION

According to the present invention there is now provided biodegradable polyanhydrides with aliphatic hydrocarbon terminals having ester or amide bonds, in combination with a substance to be released from said polyanhydrides said substance being selected from the group consisting of low molecular weight chemotherapeutic agents, peptides and proteins, anticancer agents, antibiotics, antifungals, antivirals, antiinflammatories and anticoagulants to be used for drug delivery and from the group consisting of herbicides, fertilizers and active agents useful for agriculture.

In preferred embodiments of the present invention there are provided biodegradable polyanhydrides as defined above having the formula:

R'—CO—[O—CO—R—CO]$_n$—O—CO—R' wherein R is a linear or branched organic moiety, R' is an unsaturated fatty acid with at least one cis-double bond or a non-linear hydrocarbon and n is an integer from 2 to 200.

Among the polyanhydrides included in the above formula are polyanhydrides which are novel per se and thus the present invention also provides polyanhydrides with aliphatic hydrocarbon terminals having ester or amide bonds and having the formula:

R'—CO—[O—CO—R—CO]$_n$—O—CO—R' wherein R is a linear or branched organic moiety, R' is a non-linear hydrocarbon and n is an integer from 2 to 200.

The present invention also provides methods for the preparation of the polyanhydrides.

The polymers are of controlled hydrophobicity which is affected by the ratio of the terminal groups to the polymer chain and the hydrophobicity of the terminal group (length and structure of the hydrocarbon). The polymers melt at a lower temperature, soluble in organic solvents and with low crystallinity.

In EP 0598131 there are described and claimed liquid polyanhydrides with aliphatic hydrocarbon terminals and ester bonds as cross-linking agents and as curing agents in epoxy or hydroxyl containing resins.

Said specification however does not teach or suggest the use of said polyanhydrides in combination with an active ingredient to be released therefrom such as a drug or an agent useful in agriculture and also does not teach or suggest the novel polyanhydrides having a non-linear hydrocarbon as claimed herein.

DETAILED DESCRIPTION OF THE INVENTION

As used herein, the term aliphatic refers to a linear branched of cyclic alkane, alkene or alkyne. Preferred aliphatic groups in the disclosed polyanhydrides are $C_4$ to $C_{22}$ alkyls moieties.

As used herein the term non-linear hydrocarbon refers to an alkyl chain with at least one cis-double bond or at least one more branching chain which together hydrolyze into safely eliminated molecules when implanted in a body of an animal or human.

The biodegradable compositions disclosed here are polyanhydrides which are formed by melt or solvent polycondensation of aliphatic or aromatic diacids and non-linear mono acid hydrocarbon at a 99:1 and 20:80 weight ratio. The mono acid non-linear hydrocarbons act as molecular weight controllers which limit the molecular weight to about 20,000. This relatively low but controlled molecular weight and low polydispersity, are less sensitive to depolymerization and are more stable to hydrolysis due to their hydrophobic terminals. The non-linear structure provides a range of new properties including: various degradation times and drug release profiles, reduced melting temperature and crystallinity due to irregularity induced by the bend terminals or side chains, improved mechanical strength and film forming properties by including a polyester or polyamide in the terminal side chain.

The polymers of this invention can be prepared by several methods, the diacid and mono acid molecules are refluxed together in acetic anhydride for 20 min. and the solvent is evaporated and vacuum is applied to yield the molten polymer. Alternatively, the diacid monomer and the mono acid terminal are activated by acetic anhydride to form the diacid prepolymer and the acetate anhydride derivative of the non-linear hydrocarbon which then mixed at a desired ration and polymerized at 150° C. under a vacuum of about 0.5 mm Hg. Another way of affecting polymerization is the use of a dehydrating agent that removes a water molecule from two acids to form the anhydride bond.

Biodegradable polyanhydride with ester and/or amide bonds are prepared by:

a. synthesizing a polyanhydride at a degree of polymerization (n) of 20 to 10,000;

b. reacting the polyanhydride of Step a with a polyfunctional organic molecule that contain at least two of the functional groups hydroxyl, amine, and carboxylic acid, to form polyanhydride ester and/or amide bonds with carboxylic acid terminals; and c. polymerizing the carboxylic acid terminated polymer of Step b to form a higher molecular weight polyanhydride.

The polyfunctional organic molecule that reacts with the polyanhydride to form the ester or amide bonds is selected from the group consisting of hydroxy alkyl carboxylic acid, amino alkyl carboxylic acid, dihydroxy alkane, diamino alkane, hydroxyamino alkane. Examples are: lactic acid, glycolic acid, hydroxybutyric acid, hydroxycaproic acid, hydroxybenzoic acid, ricinoleic acid, aminobenzoic acid, aminobutiric acid, natural and synthetic amino acids, ethylene diamine, butanediamine, hexanediamine, stermine, spermidine, ethylene glycol, propylene glycol, ethanol amine, butandiol; polymers of lactic acid, glycolic acid, hydroxybutyric acid, hydroxycaproic acid, ethylene glycol, propylene glycol, with hydroxyl and carboxylic acid terminals; poly(amino acids) with amino and carboxylic acid terminals; poly(ethylene glycol), poly(propylene glycol), poly(ethylene-co-propylene glycol) with amino, hydroxyl and carboxylic acid terminals; pentaeritrithol, propantriol, mucic acid, tartaric acid, and hexahydroxycyclohexane.

The method of preparation of poly(ester-anhydride) is as follows:

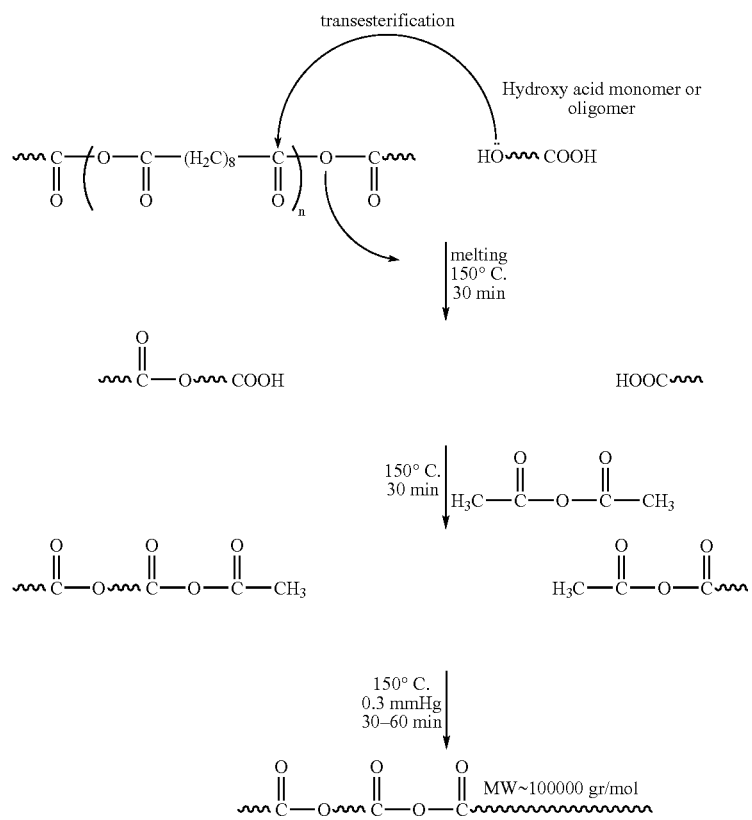

The main use for the polymers of this invention is as degradable carriers for treating local diseases such as cancer, bacterial and fungi local infections and pain. For most regional drug delivery, the drug should be administered for periods from one week to about 8 weeks. Site-specific chemotherapy that provides high drug concentrations for an extended time period in the diseased site is an effective way of treating remnant infected cells after resection of the infected area such as solid tumor. Of specific interest is the application of these polymers for site-specific chemotherapy for the treatment of solid tumors includign: squamous cell carcinoma (SCC) of the head & neck, prostate cancer, and sarcoms for intratumoral injection or insersion. Cancer of the head and neck accounts for about 40,000 new cases every year in the US which is about 5% of all new cancer cases in the US. Unlike other solid tumors, the most common manifestation of recurrence of head and neck cancer is regional, that is, recurrence in the neck.

The current treatment which include surgical removal of the tumor, systemic chemotherapy, and radiotherapy has demonstrated some effectiveness in inducing tumor regression especially in the early stage of the disease but with high rate of recurrence in the late stages. An attractive alternative is the local administration of the agent from a polymeric delivery system implanted at the site of the tumor during resection surgery. In this fashion, the drug depot can maintain a high local concentration to prevent local tumor recurrence. Also to allow the use of a variety of agents whose diffusion is not restricted by a poor blood supply secondary to a prior radiation therapy or scarring from prior surgery.

A prospective device based on the polymers of this invention is a solid or liquid polymeric implant, made of biodegradable polymer matrix loaded with an anticancer agent The effective anticancer agent, Cisplatin or Paclitaxel, is homogeneously dispersed into the polymer matrix. The active drug is released in a controlled manner to the surrounding tissue, when placed in contact with body fluids, while the polymer carrier is eliminating itself by slow degradation. The implant in a form of discs, beads, pellets, liquid polymer, or injectable microspheres is injected into the tumor or inserted into the tumor site during the surgical procedure of tumor removal. The implant is providing a high dose of anti-cancer drug for an extended period of time, in the tumor site, with minimal systemic drug distribution, thus, providing a localized treatment of the residual tumor cells as a complementary drug therapy to the surgery. For non-operable tumors, polymeric inserts can be inserted into affected tissues via invasive endoscopic techniques.

The same concept of long term drug delivery to specific diseased body sites applies also to other solid tumors, local infections such as osteomyelitis-bone infection, local anesthetic delivery to suffering cancer or AIDS patients and drugs that control tissue growth such as heparin and steroids for treating restenosis and keloids.

Dicarboxylic acid monomers: monomers useful for the synthesis of this system are aliphatic diacids of the structure: HOOC—R—COOH where R is a linear or branched chain such as: linear alkane dicarboxylic acids of $C_4$ to $C_{22}$; dimer fatty acids such as dimer erucic acid or oleic acid; non-linear fatty acid-ester derivatives such as ricinoleic acid fumarate or succinate; and cyclohexane or cyclopentane derivatives. R can be a polymeric chain with carboxylic acid terminals such as oligomers and polymers made of lactic acid, glycolic acid, hydroxy-butiric acid, caprolactone, and trimethylene carbonate having two carboxylic acid terminals.

Non-linear hydrocarbon mono carboxylic acids may include: ricinoleic acid, oleic acid, arachidonic acid, linoleic acid, linolenic acid, and other fatty acids with at least one cis-double bond; alkyl O-esters and carbonates of ricinoleic acid or hydroxystearic acid, oligo(hydroxy alkanoic acid) —O-esters and carbonates of ricinoleic acid or hydroxystearic acid; fatty acid or oligo(hydroxy alkanoic acid) esters of tartaric acid or citric acid monocarboxylic acid.

The physical properties of the polymers can be manipulated by careful selection of the degree of branching (2-4 arms), the chain length and the nature of the hydrocarbons of each arm and the content of the terminals in the polymer.

EXAMPLE 1

Synthesis and Characterization of -Alkyl Ricinoleic Acid Terminated Polyanhydrides Materials Ricinoleic acid, (85% content, technical, Fluka, Buch, Switzerland), acetic anhydride (Merck, Darmstadt, Germany), Meth-Prep II, methanol esterification reagent (Alltech, Deerfield, Ill.), were used in this study. All solvents were analytical grade from Aldrich (Milwaukee, Wis.) or Frutarom (Haifa, Israel).

Instrumentation

Infrared (IR) spectroscopy (Perkin Elmer System 2000 FT-IR) was performed on monomer, prepolymer, and polymer samples cast onto NaCl plates from dichloromethane solution. Thermal analysis was determined on a Metler TA 4000-DSC Differential Scanning Calorimeter (DSC), calibrated with Zinc and Indium standards, at a heating rate of 10° C./min. Molecular weights of the polymers were estimated on a Size Exclusion Chromatography (SEC) system consisting of a Spectra Physics (Darmstadt, Germany) P1000 pump with UV detection (Applied Bioscience 759A Absorbance UV detector) at 254 nm, a Rheodyne (Coatati, Calif.) injection valve with a 20 μl loop, and a Spectra Physics Data Jet integrator connected to a computer. Samples were eluted with $CHCl_3$ through a linear Styrogel column (Waters, 10 Å pore size) at a flow rate of 1 ml/min. The molecular weights were determined relative to polystyrene standards (Polyscience, Warrington, Pa.) with a molecular weight range of 400 to 1,500,000 using a WINner/286 computer program. $^1$H NMR spectra ($CDCl_3$) were obtained on a Varian 300 MHz spectrometer using $CDCl_3$ as solvent and tetramethylsilan (TMS) as reference. Catalytic hydrogenation was carried out with 3% palladium on carbon powder using a Parr 3911EK hydrogenation apparatus (Parr Inst. Moline Ill., USA). Fatty acid degradation products were esterified using an esterification reagent Meth-Prep II, and determined by gas chromatography (GC) using a Perkin Elmer 1020 plus GC, with a Silar 10C chromatographic column (Alltech) and FID detector using a temperature gradient of 5° C./min from 140° C. to 240° C.

Non-Linear Fatty Acid Synthesis 5 g of ricinoleic acid (17 mmole) were dissolved in 75 ml of anhydrous $CH_2Cl_2$ and placed in a 250 ml round bottomed flask. After addition of 3 ml pyridine (34 mmole) the solution was cooled to about 0° C. by immersing in an ice-water bath, and 34 mmole of the fatty acid chloride in $CH_2Cl_2$ (40 ml) were added dropwise. The mixture was warmed to room temperature and stirred for two days. The solvent was evaporated and 500 ml of anhydrous ether were added to the residue. A white precipitate was formed, which was removed by filtration. Ether was removed by rotevaporation and 100 ml of anhydrous $CH_2Cl_2$ were added. The $CH_2Cl_2$ layer was washed three times with 200 ml of aqueous $NaHCO_3$ and two times with double distilled water (DDW). The $CH_2Cl_2$ layer was dried over $MgSO_4$, and the solvent was removed by rotevaporation. Chromatography of 3 g of this product was performed on a silica gel column (60 g silica mesh 70-230) using petroleum ether/ethyl acetate (80/20 v/v) mixture as eluent to yield 1.2 g of the clean product as determined by TLC. The following esters were synthesized by this procedure:

Ricinoleic Acid stearyl Ester (Raste)

IR ($cm^{-1}$) 2900 and 2850 (C—H stretching bands), 1710 (carbonyl); $^1$H NMR 5.50 (m, 1H, $CH_2$—CH=CH—$CH_2$), 5.30 (m, 1H, $CH_2$—CH=CH—$CH_2$), 4.90 (quintet, 1H, OCO—CH), 2.50 (m, 2H, $(CH_2)_{15}$—$CH_2$—COO—CH), 2.40(m, 2H, $CH_2$—COOH), 2.30 (m, 2H, OCO—CH—$CH_2$—CH=CH), 2.00 (m, 2H, HC=CH—$CH_2$—$CH_2$), 1.60 (m, 2H, $CH_2$—$CH_2$—COOH), 1.50 (m, 2H, OCO—CH—$CH_2$—$CH_2$), 1.35 (m, 46H, 23 $CH_2$'s), 0.90 (t, 3H, Me).

Ricinoleic Acid Myristoyl Ester (Ramyre)

IR ($cm^{-1}$) 2900 and 2850 (C—H stretching bands), 1710 (carbonyl); $^1$H NMR 5.50 (m, 1H, $CH_2$—CH=CH—$CH_2$), 5.30 (m, 1H, $CH_2$—CH=CH—$CH_2$), 4.90 (quintet, 1H, OCO—CH), 2.50 (m, 2H, $(CH_2)_{15}$—$CH_2$—COO—CH), 2.40(m, 2H, $CH_2$—COOH), 2.30 (m, 2H, OCO—CH—$CH_2$—CH=CH), 2.00 (m, 2H, HC=CH—$CH_2$—$CH_2$), 1.60 (m, 2H, $CH_2$—$CH_2$—COOH), 1.50 (m, 2H, OCO—CH—$CH_2$—$CH_2$), 1.35 (m, 38H, 19 $CH_2$'s), 0.90 (t, 3H, Me).

Ricinoleic Acid Lauryl Ester (Ralaue)

IR ($cm^{-1}$) 2900 and 2850 (C—H stretching bands), 1710 (carbonyl); $^1$H NMR 5.50 (m, 1H, $CH_2$—CH=CH—$CH_2$), 5.30 (m, 1H, $CH_2$—CH=CH—$CH_2$), 4.90 (quintet, 1H, OCO—CH), 2.50 (m, 2H, (CH$_2$)$_{15}$—CH$_2$—COO—CH), 2.40(m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 34H, 17 CH$_2$'s), 0.90 (t, 3H, Me).

Ricinoleic Acid Octanoyl Ester (Raocte)

IR (cm$^{-1}$) 2900 and 2850 (C—H stretching bands), 1710 (carbonyl); $^1$H NMR 5.50 (m, 1H, CH$_2$—CH=CH—CH$_2$), 5.30 (m, 1H, CH$_2$—CH=CH—CH$_2$), 4.90 (quintet, 1H, OCO—CH), 2.50 (m, 2H, (CH$_2$)$_{15}$—CH$_2$—COO—CH), 2.40(m, 2H, CH$_2$—COOH), 2.30 (m, 2H, OCO—CH—CH$_2$—CH=CH), 2.00 (m, 2H, HC=CH—CH$_2$—CH$_2$), 1.60 (m, 2H, CH$_2$—CH$_2$—COOH), 1.50 (m, 2H, OCO—CH—CH$_2$—CH$_2$), 1.35 (m, 26H, 13 CH$_2$'s), 0.90 (t, 3H, Me).

Prepolymer Synthesis

The prepolymer of sebacic acid (SA) was prepared from the purified diacid monomer by refluxing in excess acetic anhydride for 30 minutes and evaporating the solvent to dryness. The hot clear viscous residue was dissolved in an equal volume of dichloromethane and precipitated in a mixture of ether/petroleum ether (1:1 v/v). The white precipitate was collected by filtration and dried by vacuum at room temperature. Acetyl terminated fatty acid anhydrides were prepared by dissolving the acids in acetic anhydride (120° C., 1:5 w/v) and refluxing for 20 min. Acetate anhydrides of oleic acid, linoleic acid and other cis-double bond containing fatty acid were prepared by refluxing the fatty acid in acetic anhydride for 20 min. and evaporating the solvent to dryness to obtain a liquid. Mixed prepolymers of diacids with the monoacid terminals were prepared similarly.

Polymer Synthesis

Polymers were prepared by melt condensation of the prepolymers at 150° C. [11]. Typically, fatty acid acetate anhydride (3 g) and SA prepolymer (7 g) were placed in a 50 ml round bottom flask equipped with a magnetic stirrer and a vacuum line port. The prepolymers were melted in an 180° C. oil bath before connecting the system to a vacuum line. The polymerization was continued for 1 hour under a vacuum of 0.5 mm Hg with constant stirring. The polymerization was followed by GPC analysis of samples withdrawn from the polymerization flask during polymerization. The polymers have typical IR absorption at 1740 and 1810 cm$^{-1}$ (symmetrical and asymmetrical anhydride C=O stretching bands). Terminated polymers with oleic acid, linoleic acid or linolenic acid terminals with dodecandioic acid, sebacic acid, isophthalic acid, and other diacid and triacid monomers were prepared under similar conditions to form pleable and reproducible polymers.

In Vitro Hydrolytic Degradation of Polymers

The in vitro hydrolysis was evaluated by placing rectangular samples of polymers (3×5×5 mm) (prepared by the melt casting method at 5° C. above the melting temperature of the polymer) in 10 ml of 0.1M phosphate buffer pH 7.4 at 37° C. with constant shaking (100 REV). At each time point, the polymer sample was taken out of the buffer, dried at room temperature for 2 hours and the hydrolysis of the polymer was monitored by (a) weight loss of the sample, (b) disappearance of the anhydride bonds by IR spectroscopy, and (c) changes in molecular weight of the polymer by SEC. The degradation products (fatty acids) were extracted from the aqueous phase by adding 1 ml of chloroform and vortexing for 1 min. The organic phase was collected and dried by a stream of nitrogen, followed by 2 h of lyophilization to remove all traces of water. The dry residue was dissolved in a solution mixture composed of 50 µl toluene, 10 µl methanol and 20 µl Meth-Prep II, methanol esterification reagent. The solution containing the derivatized acids was analyzed by gas chromatography using a Silar 10C chromatographic column using a temperature gradient of 5° C./min from 140 to 240° C. [12].

MRImaging

MRImaging was performed with a 4.7 T vertical Bruker Bio-Spec spectrometer (Karlsruhe, Germany). The samples (3×5×5 mm) were placed in a small glass vial containing 0.7 ml pH 7.4 Phosphate buffer and inserted into a 5 cm volume coil.

Fast spin echo T2 sequence: repetition time=300 msec, echo time=8 msec, other imaging parameters were 8 acquisitions, Slice thickness=1 mm, Field of view=4 mm, and image matrix=256×256.

In Vitro Drug Release

Methotrexate (MTX) (5 and 10 weight %) was incorporated in the polymer by mixing the drug powder in the polymer melt and cast into rectangular shapes (3×5×11 mm, 300 mg). Drug release studies were conducted by placing each polymer sample in 20 ml phosphate buffer 0.1M pH 7.2 at 37° C. with continuous shaking (100 REV). The drug concentration in the solution was determined by UV detection at 303 nm.

Polymer Stability

Stability was conducted by placing rectangular samples of polymers (3×5×5 mm) at −10° C., 4° C. and 25° C. under argon atmosphere, and monitoring the changes in molecular weight for a period of three months. The effect of the storage conditions on the drug release was determined on MTX (5 wt %) loaded polymers.

Results and Discussion

Polymer Synthesis

Ricinoleic acid was transformed into a non-linear fatty acid by esterification with fatty acid chlorides of $C_8$ to $C_{18}$ chain length in the presence of pyridine. Ricinoleic acid is a natural hydroxy fatty acid, which accounts for about 85% of the triglyceride fatty acids of castor oil, the other 15% are linear non-hydroxy fatty acids such as oleic, linoleic and stearic acid [7]. Technical ricinoleic acid [Fluka] used in this study contains about 10% of linear fatty acids, which do not form non-linear fatty acid when reacting with fatty acid chloride. Pure non-linear fatty acids were obtained by purification of the reaction product using column chromatography. $^1$H-NMR spectrum of ricinoleic acid fatty acid ester show peak at 4.9-5 ppm attributed to the methine µ to the ester, indicating successful esterification. No impurities of the ricinoleic starting material which, usually appear at 4.7 ppm (μ11 dehydration impurity), 3.6 ppm (unreacted ricinoleic acid) and 2.78 ppm (linoleic acid) are seen in the spectrum. Non-linear fatty acid terminated poly(sebacic anhydride) were synthesized by melt condensation to yield waxy off-white materials. All polymers have typical IR absorption at 1740 and 1810 cm−1 (symmetrical and asymmetrical anhydride C═O stretching bands). The physical properties of poly(sebacic acid) terminated with 30% by weight of various non-linear fatty acids with a side chain length from $C_8$ to $C_{18}$ are shown in Table I. Polymers with molecular weights in the range of 5,000 to 9,000 were obtained. The 30% w/w content of the non-linear fatty acid was chosen since it was previously found that up to this ratio, the final product is mainly fatty terminated polymer with up to about 5% w/w of the symmetric fatty anhydride. Above this ratio, the molecular weight dropped to a level of 2000-3000 and the percent of the symmetric anhydride increased to 10-40% [8]. All terminated polymers melted at temperatures between 70 and 79° C., which makes them suitable for drug incorporation by melt molding process. The heat capacity values (μH) of all polymers were lower to that of PSA (68-80 J/g), which indicates that these non-linear fatty terminated polymers are less crystalline relative to poly(sebacic acid). This effect is attributed to the presence of the ricinoleic acid based non-linear terminals. When PSA was terminated with 30% (W/W) ricinoleic acid acetyl ester a value of 45 J/g was obtained.

In Vitro Hydrolysis of Polymers

The hydrolysis of the terminated polymers was studied in comparison with PSA acetate terminated by monitoring the weight loss, hydrolysis of anhydride bonds, and change in polymer molecular weight during hydrolysis. The weight average molecular weight of the degraded samples were monitored by SEC, a sharp decrease in molecular weight was observed during the first 48 h, followed by a slow degradation phase which kept the Mw at 3000 for another 7 days. PSA lost about 70% of its initial weight after 6 days, during this period the non-linear fatty acid terminated polymers lost up to 40% of their initial weight. The period of mass loss starts when the polymer molecular weight reaches a number average molecular weight (Mn) of about 2,000, regardless of the initial molecular weight of the polymer. During this period which last for about one week, the relatively water soluble component, sebacic acid, is released from the wafer leaving the hydrophobic component, ricinoleic acid based non-linear fatty acid, which is slow to solubilize.

In Vitro Drug Release from the Polymers

The release characteristics of drugs from these non-linear fatty acid terminated polyanhydrides were determined using methotrexate (MTX) as a model drug. At earlier stages MTX was released at the same rate from all the polymers. After 3 days the release is depended on the length of the fatty acid side chain, the longer the side-chain the slower is the release. This data correlates with the data obtained from the degradation studies that showed that during the period of 3 to 7 days the device contains higher amounts of the hydrophobic non-linear fatty acid which retard water from penetrating into the polymer matrix to cleave the labile anhydride bonds and release the drug.

The rate of drug release increased linearly with loading, and identical release profile were found for both concentrations also attribute to the surface erosion process. It was previously reported [15, 16] that since the penetration of water into the polymer matrix is the key event in the release of the drug and the degradation of the polymer, MRI offer a potentially valuable tool for following this process. MRI images of eroding P(RAMYRE:SA) loaded with 5% MTX were taken. Bright areas on the images indicates high amount of water, no MRI images were attainable with dry tablets. One of the advantages of the MRI technique is that the detected device can be virtually sliced to a very thin slices and each slice can be analyzed for water penetration. At t=0 both slices are black since water did rot penetrate into the device. In the contrary after two days in buffer solution, a signal enhancement from outside to the inside of the polymer was observed. The surface of the polymer (slice No. 1) is composed mainly from white and gray areas where in the second slice the core is absolutely black indicating that water did not penetrate yet but the edges that were exposed to water do absorb some water. This data combined with the visual observation of the device, which indicated a porous white solid and fragile eroding zone, indicates that the polymer degradation and drug release is mainly due to surface erosion front mechanism [17]. This mechanism is characterized with degradation occurring in a region of finite thickness of the device known as the erosion zone. This zone is a dynamic region where degradation occurs while at the intact zone, (the inner area) degradation proceeds slowly or does not take place at all.

Polymer Stability

Polyanhydrides are considered as air sensitive material and are usually stored at −20° C. under argon atmosphere. The stability of blank and MTX-loaded formulations of non-linear fatty acid terminated PSA was studied. Three rectangular samples packed in glass bottles under argon atmosphere were stored at −10, 4 and 25° C. and the molecular weight, drug content and drug release rate were determined. For both, the blank and MTX loaded polymers, the molecular weight remained between 7,000 and 10,000 throughout the first 40 days at −10 and 4° C., while a slight drop of the initial value for the samples stored at 25° C. was observed. The polymer retained its initial molecular weight for 1 year at −10° C. and for six months at 4° C. In contrary, PSA without terminating fatty acids retained its initial molecular weight only at −10° C., while at the other two temperatures the molecular weight dropped much faster than the terminated PSA. Polyanhydrides may decrease in molecular weight during storage either as a result of hydrolysis caused by entrapped water during preparation or from penetration of water vapors into the package during storing. Under freezing temperature (−10° C.) there is minimal active water to cause anhydride hydrolysis, thus both terminated and non-terminated PSA retained their initial molecular weight. This is not the case at the other two temperatures, nonlinear terminated PSA kept its initial molecular weight for 3 weeks at room temperature, and for 6 months at 4° C. The insertion of non-linear hydrophobic side chains into the polymer backbone increases its hydrophobicity which, retards water from penetrating into the polymer mass and decreasing its molecular weight. The decrease in molecular weight after 40 days at room temperature did not affect the release profile of MTX from the non-linear fatty acid terminated polymers. Similar results were obtained for other polyanhydrides, where matrices prepared from polymers of molecular weights ranging from 10,000 and 50,000 degraded and released the incorporated drug for a similar time period [7, 18].

ture. Low molecular weight L-PLA and DL-PLA were prepared from the corresponding lyophilized lactic acids by condensation reaction at 180° C. The hot light brown clear viscous residue was dissolved in an equal volume of $CHCl_3$ and precipitated in a mixture of diisopropyl ether/petroleum ether (9:1 v/v). The white precipitate was collected by filtration and dried in vacuo at room temperature. Low molecular weight D-PLA was prepared from the correspond-

TABLE I

Molecular weight and melting temperature of non-linear fatty acid terminated poly(sebacic anhydride)

| Polymer | Mw | Mn | Tm (° C.) | μH (J/g) |
|---|---|---|---|---|
| P(RASTE:SA)3:7 – X = 16 | 7,300 | 5,000 | 79.0 | 64.6 |
| P(RAMYRE:SA)3:7 – X = 12 | 9,000 | 6,400 | 77.5 | 68.1 |
| P(RALAUE:SA)3:7 – X = 10 | 7,600 | 5,400 | 78.2 | 79.0 |
| P(RAOCTE:SA)3:7 – X = 6 | 6,600 | 4,400 | 77.1 | 67.1 |
| P(RAACE:SA)3:7 – X = 0 | 5,000 | 4,000 | 73.1 | 44.7 |

Mw and Mn were determined by SEC, Tm and μH were recorded by DSC at 10° C./min.

EXAMPLE 2

Synthesis of Oleic Acid Terminated Polyanhydrides

Oleic acid was mixed with the following diacids: sebacic acid, ricinoleic acid maleate, polyethylene glycol dicarboxylic acid (Mw=1000), isophthalic acid, terephthalic acid, fumaric acid, poly(lactic acid) dicarboxylic acid (Mw=1700), poly(lactic-glycolic acid) (Mw=1500), and polycaprolactone dicarboxylic acid (Mw=2000). The amount of oleic acid increased from 5% by weight to 30% and the mixtures were dissolved in acetic anhydride (1:10 w/w) and refluxed for 30 min. The solvent was evaporated to dryness and the residue was vaccume polymerized at 150° C. for 2 hours (0.1 mm Hg) to form a viscouse melt which solidified at room temperature. The melting points of the various polymers ranged from 30 to 65° C.

Polymers with mixed terminals were prepared by mixing the oleic acid with non-linear or linear mono carboxylic acids to obtain polymers with different physical and mechanical properties.

EXAMPLE 3

Preparation of Triblock PLA-PSA Copolymers

Sebacic acid prepolymer was prepared from the purified diacid monomer by refluxing in excess acetic anhydride for 30 min and evaporating the solvent to dryness.

The hot clear viscous residue was dissolved in an equal volume of dichloromethane and precipitated in a mixture of ether/petroleum ether (1:1 v/v). The white precipitate was collected by filtration and dried in vacuo at room temperaing hydrolyzed and lyophilized D-Lactide, the followed synthesis and purification was the same as for L and DL-PLA. The oligomerization was followed by GPC, H-NMR and IR analysis. The NMR for L-PLA [$^1$H NMR ($CDCl_3$/TMS,δ): 1.5 ($CH_3$ due to the hydroxyl terminal of the 2-hydroxypropionate unit), 1.6 ($CH_3$ for the I-lactate unit), 4.4 (CH due to the hydroxyl terminal of the 2-hydroxypropionate unit), 5.2 (CH for the I-lactate unit)]. From the integral ratio of the methyne signal at δ=4.4 ppm relative to that at δ=5.2 ppm, the degree of polymerization was found to be 30, and the number average molecular weight was about 2200 Da, supported by GPC.

Acetyl terminated and symmetric poly(lactic) acid anhydrides were prepared by dissolving low molecular weight PLA in acetic anhydride (120° C., 1:5 w/v) and refluxing for 20 min.

Polymers were prepared by melt condensation of the prepolymers at 150° C. to yield off-white materials, in different PLA acetate anhydride and SA prepolymer ratios. Both prepolymers were placed in a 50-mL round bottom flask equipped with a magnetic stirrer and a vacuum line port. They were melted in a 180° C.-oil bath before connecting the system to a vacuum line. The polymerization was continued for approximately 1 h, at 0.5 mmHg, with constant stirring [FIG. 1 (Part 1)]. The polymerization was followed by GPC analysis of samples withdrawn during polymerization. All polymers posses typical IR absorption at 1740 and 1810 cm which correspond to symmetrical and asymmetrical anhydride carbonyl stretching bands where the absorption at 1740 correspond also to the ester carbonyl stretching bands.

The NMR for L-PLA-PSA 60:40 [$^1$H NMR (CDCl$^3$/TMS, δ): 1.5 (CH$_3$ due to the hydroxyl terminal of the 2-hydroxypropionate unit), 1.6 (CH$_3$ for the I-lactate unit), 4.4 (CH due to the hydroxyl terminal of the 2-hydroxypropionate unit), 5.2 (CH for the I-lactate unit) for PLA terminals. And for Sebacic acid 1.32 for (4H) —COOCO—CH$_2$—CH$_2$—, 2.3-2.5 for (2H) —COOCO—CH$_2$—CH$_2$—].

The drug-release characteristics from these PLA terminated polyanhydrides and their stereocomplexes were determined using Triamcinolone (TRIAMCINOLONE) as representative of hydrophobic drug and 5-Fluoro-Uracil (5-FU) as representative of hydrophilic drug. Both drugs were released constantly for periods from one week to three weeks depending on the ratio of PLA and anhydride blocks. PLA terminated polyanhydride segments made of diacid monomers including: suberic acid, undecandioic acid, terephthalic acid, 1.5-furan dicarboxylic acid, and ricinoleic acid succinate were prepared using these procedures.

EXAMPLE 4

Preparation of Multiblock PLA-PSA Copolymers by Transesterification.

Random PLA-PSA copolymer with multiple PLA and PSA blocks. Using this method, any hydroxy acid oligomers are used for the transesterification.

Typically PSA (30,000 Da) and PLA (700-1100 Da) are placed in 50 mL round bottomed dry flask equipped with magnetic stirrer, condenser and CaCl$_2$ tube. The polymers are dissolved in minimal amount of dichloromethane. The solution is refluxed for 4-5 hours. The solvent is evaporated till dryness. The residue is off-white wax. The solid is melted in oil bath in 150° C. and stirred for more 30 min in order to complete the trans-esterification. Acetic anhydride is added (1:1 w/v) and the heating continues for one hour. The flask is connected to a vacuum line (0.5 mm Hg) at 150° C. for 2 hours (or till the maximal molecular weight is obtained).

In Vitro Hydrolytic Degradation of Polymers

The hydrolysis of the polymers was evaluated by placing rectangular samples of polymer (3×5×5 mm, 100 mg ) in 10 mL 0.1M phosphate buffer pH 7.4 at 37° C. with continuous shaking (100 rpm). At each time point polymer sample was taken out of the buffer and dried under vacuum at room temperature overnight. The hydrolysis of the polymer was monitored by (a) weight loss of the sample, (b) disappearance of the anhydride bonds by IR spectroscopy, (c) changes in polymer molecular weight as determined by GPC, (d) Lactic acid release by reagent lactate. All experiments were carried out in triplicates.

EXAMPLE 5

Poly(Ester-Anhydrides)

Transesterification of poly(sebacic acid) (PSA) is a one-pot reaction that starts with a high molecular weight polymer based on anhydride bonds and yields polymer based on random anhydride ester bonds. In order to convert poly (anhydride) to poly(ester-anhydride) we react the polymer with hydroxy fatty acid (HFA). The hydroxyl group of HFA attacks the anhydride bond in a transesterification reaction. The products of the reaction are carboxyl group ended olygomers based one pure anhydride bonds or random mixed ester anhydride bonds.

In principal, any hydroxy alkyl acid is suitable for that type of reaction. The purpose of the final product (biodegradable polymer for suspended drug delivery) limits us to non-irritant and pure hydroxy acids. Conditions of the reaction dictate another limitation—melting point below 200° C. or solubility in common organic solvents. The list of hydroxy acids include: lactic acid or its oligomers, glycolic acid or its olygomers, ricinoleic acid, lithocholic acid, and hydroxybenzoic acid. That study focuses on two hydroxy fatty acids: ricinoleic acid and lithocholic acid. Ricinoleic acid (D-12-hydroxyoctadec-cic-9-enoic acid) is a hydroxylated fatty acid that accumulates in the seeds of castor been (*Ricinus communis* L.) plants and ather species. Technical ricinoleic acid (Fluka) used in that study contains about 15% of linear and not linear fatty acids, which do not contain hydroxyl group therefor can not react in transesterification reaction.

Lithocholic acid is bile acid. Bile acids are natural, amphiphilic compounds stored in the gallbladder and serve as emulsifiers for solubilization of fats and lipids in food. When such biocompounds are used in the preparation of polymer materials, they should be better tolerated in the biological environment, especially in the gastrointestinal tract.

As known, fast eroding polymers are suitable candidates to control drug release through erosion mechanism. Those are polymers that have a fast hydrolyzing bond such as polyanhydrides. Incorporation of ester bonds into anhydride framework reduces the hydrolysis, because ester bonds hydrolyze slower then anhydride. Still said polymers have all the properties of a biodegradable polymer that anhydride bonds provide. Thus there is provided a surface eroding polymer with longer degradation time.

Materials

Ricinoleic acid, technically 85% pure (Fluca, Buch, Switzerland); sebacic acid 99% pure and lithocholic acid 98% (Aldrich Milwaukee, Wis.); acetic anhydride (Merck, Darmstadt, Germany) were used in this study. All solvents were analytical grade from Aldrich (Milwaukee, Wis.) or Frutarom (Haifa, Isral).

Procedure

The prepolymer of sebacic (SA) acid was prepared from purified diacid monomer by refluxing in excess (1:5 w/v) acetic anhydride for 30 min with constant stirring and evaporating the solvent to dryness. The hot clear viscous residue was dissolved in an equal volume of dichloromethane (DCM) and precipitated in a mixture of ether/petroleum ether (1:1 v/v). The white precipitate was collected by filtration and dried by vacuum at room temperature. The polymer of SA (PSA) was prepared by melt condensation of the prepolymer at 160° C. The polymerization was continued for 3 hours under a vacuum of 0.1 mmHg with constant stirring. The polymerization was followed by GPC analysis of samples withdrawn from the polymerization flask during polymerization every 30 min.

The final molecular weight was 36000. The polymer has typical IR absorption at 1740 and 1810 cm$^{-1}$ (symmetrical and asymmetrical anhydride C=O stretching bands.

The poly(ester-anhydrides) were prepared in a one-pot reaction in two steps: (a) transesterification: typically, PSA and hydroxy acid were dissolved in excess toluene in dry 100 ml round-bottomed flask equipped with a mechanical stirrer and Dean-Stark glassware. The reaction took place at 120° C. followed by GPC analysis of withdrawn from the reaction flask during the reaction. The reaction was stopped as soon as the product achieved minimal stable molecular weight (according to the theory). The duration of the transesterification reaction was 1.5-3 hours depending on the kind and percentage of hydroxy acid. (b) polymerization: the off-white paste product (prepolymer) was dissolved in acetic anhydride (1:1 w/v) and refluxed for 30 min. The solvent was evaporated to dryness. The poly(ester-anhydrides) were prepared by melt condensation of the prepolymer at 160° C. The polymerization was continued for 1.5-4 hours under a vacuum of 0.1 mmHg with constant stirring. Duration of the polymerization depended on theoretical molecular weight of the final product. The polymerization was followed by GPC analysis of samples withdrawn from the polymerization flask during polymerization every 30 min. All solid polymers of that family melted at temperatures between 64 and 77° C. which makes them suitable for drug incorporation via melt molding process. The melting point of lithocholic acid based poly(ester-anhydrides) was higher than of the corresponding ricinoleic acid based poly(ester-anhydrides). Ricinoleic acid based poly(ester-anhydrides) are yellow solids for PSA-RA ratios 9:1-5:5. PSA-RA 6:4 polymer is waxy and very viscose. PSA-RA 3:7 and 2:8 polymers are pasty and suitable for injection. Lithocholic acid based poly(ester-anhydrides) are solid for all ratios PSA-LitA 9:1-2:8. All polymers of that family are film forming. They are very elastic and flexible.

Spectroscopy Analysis

All the polymers of that kind have typical IR absorption at 1740 and 1810 cm$^{-1}$ (symmetrical and asymmetrical anhydride C=O stretching bands and at 1050-1300 cm$^{-1}$ (ester C—O stretching bands). All the ricinoleic acid based poly(ester-anhydrides) have typical NMR peaks at 4.95 ppm (quintet, 1H OCO—CH) and at 2.43 ppm (triplet, 6H (2H of ricinoleic acid and 4H of sebcic acid) CH$_2$—CH$_2$—COOCO). Those peaks indicate presence of ester and anhydride bonds in the product. All the spectrum lacks a peak at 3.64 ppm (m, 1H CH$_2$—CHOH—CH$_2$). According to NMR spectrum there is no free ricinoleic acid in the final product.

The molecular weights and melting temperatures of the polymers is given in the following tables:

| ratio | index | Mn | Mw | m.p. |
|---|---|---|---|---|
| p(PSA-LitA) 3:7 | PA-MK-138i | 8363 | 21172 | 200-211 |
| p(PSA-LitA) 4:6 | PA-MK-138iii | 11155 | 44235 | 101-110 |
| p(PSA-LitA) 5:5 | PA-MK-138iii | 17241 | 130512 | 89-96 |
| p(PSA-LitA) 6:4 | PA-MK-139ii | 9840 | 24978 | 56-60 |
| p(PSA-LitA) 7:3 | PA-MK-134iii | 14634 | 93818 | 57-69 |
| p(PSA-LitA) 9:1 | PA-MK-127iii | 9976 | 13074 | 54-58 |

In this table: p(PSA-Lia) is a polyanhydride ester made from polysebacic anhydride reacted with lithacolic acid and various weight ratios. All polymers are solids.

The molecular weights and melting points of the poly (anhydride-ester) of ricinoleic acid-sebacic acid are as follows:

| ratio | index | Mn | Mw | m.p. |
|---|---|---|---|---|
| p(PSA-RA) 9:1 | PA-MK-129i | 9923 | 20994 | 72-75 |
| p(PSA-RA) 8:2 | PA-MK-129ii | 11195 | 21094 | 73-75 |
| p(PSA-RA) 7:3 | PA-MK-141iii | 20820 | 60307 | 65-69 |
| p(PSA-RA) 6:4 | PA-MK-141ii | 10574 | 30286 | 55-62 |
| p(PSA-RA) 5:5 | PA-MK-141i | 8117 | 19625 | 53-56 |
| p(PSA-RA) 3:7 | PA-MK-137i | 8463 | 9002 | Liquide |
| p(PSA-RA) 2.5:7.5 | PA-MK-137ii | 2179 | 2300 | Liquide |
| p(PSA-RA) 2:8 | PA-MK-137iii | 1842 | 2146 | Liguide |

The ricinolecic acid-sebacic acid anhydride-ester copolymers are solids or liquids at room temperature depending on the ricinoleic acid content.

In vitro release of drugs from polymers:

Solid and liquid polymers of this invention were used for the release of cisplatin, methotrexate, paclitaxel and 5-fluorouracil from the polymers. Solid implants were prepared by melt mixing the drug at a 5% and 10% w/w and cast into cylindrical devices of 5 mm in diameter and 3 mm hight. Liquid polymers were mixed with the drugs and loded into syringes. The following polymers were used: P(PSA-RA) anhydride-ester of 30 and 50% are solids and 70, 75, and 80% w/w ricinoleic acid content are liquids. All formulations released the incorporated drug in a controlled manner for 10 to 18 days depending on the polymer composition. The liquid polymers formed a semi-solid structure after addition to the phosphate buffer solutions. The liquid polymers prepared from ricinoleic acid terminated poly(sebacic acid) with 70 and 80% ricinoleic acid terminals released the drugs for only 4 to 7 days.

The cisplatin loaded polymers are suitable for treating cancer in vivo. In an in vivo experiment, mice induced withsolid cancer (SCC head and neck cancer cells) were treated with the polymer implant injected or inserted near the solid tumor and showed a regression in size of the tumor 4 weeks after implantation. The polymers were biodegradable and biocompatible.

EXAMPLE 6

Poly(Anhydride Amide)

Polyanhydride amide are synthesized using a similar procedure but amino acid such as glycine or b-alanine is used to react with poly(suberic anhydride) for 3 hours in toluene. The resulted dicarboxylic acid anhydride-amide oligomers are polymerized into a polyanhydride by reacting the oligomers with acetic anhydride with further vaccume. The resulted polymer contain amide bonds and anhydride bonds at a ratio corresponding to the amount of amino acid reacted.

Similarly, hydroxyl amine or polyethylene glycol were reacted with poly(sebacic acid) to form poly(ester anhydride) or poly(ester-amide anhydride). These polymers are of good mechanical properties, film forming and release drugs for periods from one to four weeks.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

REFERENCES

1. Domb, A. J.; Amselem, S.; Langer, R.; Maniar, M. In *Designed to Degrade Biomedical Polymers*, Shalaby S.; Ed.; Carl Hauser Verlag, 1994; p 69.
2. Domb, A. J.; Elmalak, O.; Shastry, V. R.; Ta-Shma, Z.; Masters, D. M.; Ringel, I.; Teomim, D.; Langer, R. In *Handbook of biodegradable polymers*, Domb, A. J.; Kost, J., Weiseman, D. M.; Eds.; Hardwood academic publishers, 1997, p 135.
3. Rosen, H. B.; Chang, J.; Wnek, G. E.; Lindhardt, R. J.; Langer, R, *Biomaterials.*, 1983, 4, 131.
4. Domb, A. J.; Gallardo, C. E.; Langer, R. *Macromolecules*, 1989, 22, 3200.
5. Bremer, J.; in *Fatty acid metabolism and its regulation*, Numa, S.; Ed.; Elsevier, 1984; p 113.
6. Domb, A. J.; Maniar, M. *J. Poly. Sci.: Polymer Chem.* 1993, 31, 1275.
7. Teomim, D.; Nyska, A.; Domb, A. J. *J. Biomed Mater Res*, 1999, 45, 258-287.
8. Teomim, D.; Domb, A. J. *J. Polym. Sci.*, 1999, 37, 3337.
9. Park, E. S.; Maniar, M.; Shah J. C. *J. Control. Rel.* 1998, 52, 179.
10. Teomim, D.; Fishbein, I.; Golomb, G.; Orllof, L. A.; Mayberg, M.; Domb, A. J. *J. Control .Rel*, 1999, 60, 129.
11. Domb, A. J.; Langer, R. *J. Polym. Sci. Polym. Chem.* 1987, 25, 3373.
12. Tirosh, O.; Cohen, R.; Catzhendler, J.; Alon, A.; Barenholz, Y. *Chemistry and physics of lipids*, 1997, 87,17-22.
13. Heller, J. *CRS Crit. Rev. Ther. Drug Carrier Syst.*, 1984, 1,39.
14. Hopfenberg, H. M.; in Controlled release polymeric Formulation, Paul, D. R.; Harris, F. W. Eds.;,ACS Symposium series, ACS, Washington D.C., 1976, 33, 26.
15. Mader, K.; Cremmilleux, Y.; Domb, A. J.; Dunn, J. F.; Swartz, H. M. *Pharm. Res*, 1997, 14(6), 820.
16. Mader, K.; Bacic, G.; Domb, A. J.; Elmalak, O.; Langer, R.; Swartz, H. M. *J. Pharm. Sci*, 1997, 86, 126.
17. Gopferich, A. in In *Handbook of biodegradable polymers*, Domb, A. J.; Kost, J.; Weiseman, D. M.; Eds.; Hardwood academic publishers, 1997, p451.
18. Dang, W.; Daviau, T.; Ying, P.; Zhao, Y.; Nawotnik, D.; Clow, C. S.; Tylor, B.; Brem, H. *J. Controlled Rel.*, 1996 42, 83.

What is claimed is:

1. A biodegradable aliphatic polyanhydride multiblock copolymer comprising random ester or amide bonds along the polymer chain,
synthesized by the polymerization of a polyanhydride formed of an aliphatic dicarboxylic acid with a degree of polymerization (n) of 20 to 10,000, reacted with a polyfunctional organic molecule that contains at least two functional groups selected from the group consisting of hydroxyl, amino, carboxylic acid, and combinations thereof.

2. The polyanhydride of claim 1, wherein in the polyanhydride comprises a monomer derived from a compound selected from the group consisting of $C_4$-$C_{22}$ alkane dicarboxylic acids, fumaric acid, itraconic acid, dimer oleic acid, dimer erucic acid, ricinoleic acid, diacids of ricinoleic acid O-esters selected from the group consisting of ricinoleic acid fumarate and succinate, and mixtures thereof.

3. The polyanhydride of claim 1, wherein the polyfunctional organic molecule is selected from the group consisting of hydroxy alkanoic acids, amino alkanoic acids, dihydroxy alkanes, diamine alkanes, and hydroxyamino alkanes.

4. The polyanhydride of claim 3, wherein the hydroxy alkanoic acid is selected from the group consisting of lactic acid, glycolic acid, hydroxybutyric acid, hydroxycaproic acid, ricinoleic acid, ethylene glycol or propylene glycol with hydroxyl and carboxylic acid terminals, poly(ethylene glycol), poly(propylene glycol), and poly(ethylene-co-propylene glycol) with terminals selected from the group consisting of amino, hydroxyl and carboxylic acid groups, and combinations thereof.

5. The polyanhydride of claim 3, wherein the amino alkanoic acid is selected from the group consisting of aminobutyric acid, natural and synthetic amino acids, and combinations thereof.

6. The polyanhydride of claim 3, wherein the diamino alkane is selected from the group consisting of ethylene diamine, butanediamine, hexanediamine, stermine, spermidine, and combinations thereof.

7. The polyanhydride of claim 4, wherein the polymer comprises at least 70% w/w ricinoleic acid.

8. The polyanhydride of claim 7, wherein the polyanhydride is an injectable polymer.

9. The polyanhydride of claim 7, wherein the polymer is adapted to form a semi-solid structure after addition to a buffer solution.

10. The polyanhydride of claim 1 obtainable by:
 (a) synthesizing a polyanhydride from an aliphatic dicarboxylic acid with a degree of polymerization (n) of 20 to 10,000;
 (b) reacting with a polyanhydride of step (a) with a polyfunctional organic molecule that contains at least two functional groups selected from the group consisting of hydroxyl, amino, carboxylic acid, and combinations thereof, to form a polyanhydride comprising ester and/or amide bonds and terminated with carboxylic acid groups; and
 (c) polymerizing the carboxylic acid terminated polymer of step (b) to form a higher molecular weight aliphatic polyanhydride.

11. The polyanhydride of claim 10, wherein the aliphatic dicarboxy acid is selected from the group consisting of $C_4$-$C_{22}$ alkane dicarboxylic acids, fumaric acid, itraconic acid, dimer oleic acid, dimer erucic acid and diacids of ricinoleic acid O-esters selected from the group consisting of ricinoleic acid fumarate and succinate, and mixtures thereof.

12. The polyanhydride of claim 10, wherein the polyfunctional organic molecule is selected from the group consisting of hydroxy alkanoic acids, amino alkanoic acids, dihydroxy alkanes, diamino alkanes, and hydroxyamino alkanes.

13. The polyanhydride of claim 12, wherein the hydroxy alkanoic acid is selected from the group consisting of lactic acid; glycolic acid; hydroxybutyric acid; hydroxycaproic acid; ricinoleic acid; ethylene glycol or propylene glycol with hydroxyl and carboxylic acid terminals; poly(ethylene glycol), poly(propylene glycol), and poly(ethylene-co-propylene glycol) with terminals selected from the group consisting of amino, hydroxyl and carboxylic acid groups; and combinations thereof.

14. The polyanhydride of claim 12, wherein the amino alkanoic acid is selected from the group consisting of aminobutyric acid, natural and synthetic amino acids, and combinations thereof.

15. The polyanhydride of claim 12, wherein the diamino alkane is selected from the group consisting of ethylene diamine, butanediamine, hexanediamine, stermine, spermidine, and combinations thereof.

16. A composition for delivery of a bioactive or bioreactive molecule, the composition comprising the biodegradable aliphatic polyanhydride multiblock copolymer of claim 1 and a bioactive or bioreactive molecule, wherein the bioactive or bioreactive molecule is released from the polyanhydride carrier.

17. The composition of claim 16 wherein the bioactive or bioreactive agent is selected from the group consisting of anticancer agents, antibiotics, antifungals, antivirals, antiimflammatories, anticoagulants, herbicides, fertilizers, and combinations thereof.

18. The composition of claim 16 wherein the bioactive or bioreactive molecule is selected from the group consisting of low molecular weight chemotherapeutic agents and peptides and proteins.

19. The composition of claim 16, wherein the polymer comprises at least 70% w/w ricinoleic acid.

20. The composition of claim 19, wherein the polyanhydride is an injectable polymer.

21. The composition of claim 19, wherein the polymer forms a semi-solid structure after addition to a buffer solution.

22. The composition of claim 19, wherein the bioactive agent is one or more anti-cancer agents.

23. The composition of claim 19, wherein the anti-cancer agent is selected from the group consisting of platinum derivatives, taxanes and anti-metabolites.

24. The composition of claim 19, wherein the polyanhydride in combination with the anti-cancer agent is in a form suitable for injection or insertion near or into a solid tumor.

25. A method for the preparation of a biodegradable aliphatic polyanhydride multiblock copolymer comprising random ester or amide bonds on the polymer chains the method comprising (a) synthesizing a polyanhydride from a dicarboxylic acid with a degree of polymerization (n) of 20 to 10,000;

(b) reacting the polyanhydride of step (a) with a polyfunctional organic molecule that contain at least two of the functional groups hydroxyl, amine, and carboxylic acid, to form polyanhydride ester and/or amide bonds with carboxylic acid terminals; and (c) polymerizing the carboxylic acid terminated polymer of step (b) to form a higher molecular weight polyanhydride.

26. The method of claim 25, wherein the polyanhydride is prepared from a dicarboxylic acid selected from the group consisting of $HOOC-(CH_2)_{4-22}COOH$, fumaric acid, itraconic acid, dimer oleic acid, dimer erucic acid and diacids of ricinoleic acid O-esters selected from the group consisting of acid fumarate and succinate, dicarboxylic acid derivatives of oligomers and polymers of hydroxy acids, including lactic acid, glycolic acid, caprolactone, and hydroxy butyric acid and mixtures thereof.

27. The method of amino 25, wherein the polyfunctional organic molecule is selected from the group consisting of hydroxy alkanoic acids, amino alkanoic acids, dihydroxy alkanes, diamino at alkanes, and hydroxyamino alkanes.

28. The method of claim 27, wherein the hydroxy alkanoic acid is selected from the group consisting of lactic acid, glycolic acid, hydroxybutyric acid, hydroxycaproic acid, ricinoleic acid, ethylene glycol or propylene glycol with hydroxyl and carboxylic acid terminals, poly(ethylene glycol), poly(propylene glycol), and poly(ethylene-co-propylene glycol) with terminals selected from the group consisting of amino, hydroxyl and carboxylic acid groups, and combinations thereof.

29. The method of claim 27, wherein the amino alkanoic acid is selected from the group consisting of aminobutyric acid, natural and synthetic amino acids, and combination thereof.

30. The method of claim 27, wherein the diamino alkane is selected from the group consisting of ethylene diamine, butanediamine, hexanediamine, stermine, spermidine, and combinations thereof.

31. The method of claim 27, wherein the diamino alkane is selected from the group consisting of ethylene diamine, butanediamine, hexanediamine, stermine, spermidine, and combinations thereof.

* * * * *

UNITED STATES PATENT AND TRADEMARK OFFICE
CERTIFICATE OF CORRECTION

PATENT NO. : 7,297,347 B2  Page 1 of 1
APPLICATION NO. : 10/433143
DATED : November 20, 2007
INVENTOR(S) : Abraham J. Domb It is certified that error appears in the above-identified patent and that said Letters Patent is hereby corrected as shown below:

Claim 3, column 22, line 15, replace "diamine" with --diamino--.

Claim 11, column 22, line 55, replace "dicarboxy" with --dicarboxylic--.

Claim 23, column 23, line 38, replace "19" with --22--.

Claim 24, column 23, line 41, replace "19" with --22--.

Claim 26, column 24, lines 15-16, replace "consisting of acid" with --consisting of ricinoleic acid--.

Signed and Sealed this

Tenth Day of June, 2008

JON W. DUDAS
*Director of the United States Patent and Trademark Office*